United States Patent
Ortigosa et al.

(10) Patent No.: US 11,198,718 B2
(45) Date of Patent: Dec. 14, 2021

(54) PURIFYING INSULIN USING CATION EXCHANGE AND REVERSE PHASE CHROMATOGRAPHY IN THE PRESENCE OF AN ORGANIC MODIFIER AND ELEVATED TEMPERATURE

(71) Applicant: Merck Sharp & Dohme Corp., Rahway, NJ (US)

(72) Inventors: Allison D. Ortigosa, Harrisonburg, PA (US); Michael P. Coleman, West Point, PA (US); Shibu T. George, Thorton, CO (US); Michael A. Rauscher, Garwood, NJ (US); Mark C. Sleevi, Longmont, CO (US); Kartoa Chow, San Francisco, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 31 days.

(21) Appl. No.: 16/551,974

(22) Filed: Aug. 27, 2019

(65) Prior Publication Data
US 2020/0010525 A1    Jan. 9, 2020

Related U.S. Application Data

(63) Continuation of application No. 15/124,080, filed as application No. PCT/US2015/019864 on Mar. 11, 2015, now Pat. No. 10,407,483.

(60) Provisional application No. 61/953,001, filed on Mar. 14, 2014.

(51) Int. Cl.
  *C07K 14/62* (2006.01)
  *C07K 1/18* (2006.01)
  *C07K 1/20* (2006.01)

(52) U.S. Cl.
  CPC .............. *C07K 14/62* (2013.01); *C07K 1/18* (2013.01); *C07K 1/20* (2013.01)

(58) Field of Classification Search
  CPC ............ C07K 14/62; C07K 1/18; C07K 1/20
  See application file for complete search history.

(56) References Cited

U.S. PATENT DOCUMENTS

| | | |
|---|---|---|
| 5,473,049 A | 12/1995 | Obermeier et al. |
| 5,621,073 A | 4/1997 | Dickhardt |
| 5,663,291 A | 9/1997 | Obermeier et al. |
| 5,977,297 A | 11/1999 | Obermeier et al. |
| 5,986,048 A | 11/1999 | Rubroder et al. |
| 6,265,542 B1 | 7/2001 | Fahrner et al. |
| 6,380,355 B1 | 4/2002 | Rubroder et al. |
| 6,710,167 B1 | 3/2004 | Sievers et al. |
| 2006/0222698 A1 | 10/2006 | Lau et al. |
| 2011/0040075 A1 | 2/2011 | Bonnerjea et al. |
| 2012/0214965 A1 | 8/2012 | Zimmerman et al. |

FOREIGN PATENT DOCUMENTS

| | | |
|---|---|---|
| EP | 0849277 | 6/1998 |
| EP | 1666048 | 6/2006 |
| WO | 2000055184 | 9/2000 |

*Primary Examiner* — James H Alstrum-Acevedo
*Assistant Examiner* — Erinne R Dabkowski
(74) *Attorney, Agent, or Firm* — John David Reilly; Anna Cocuzzo

(57) ABSTRACT

A process is described for purifying insulin and insulin analogs that comprises high-pressure liquid chromatography with an acidic cation exchange medium performed in the presence of a water miscible organic modifier and at an elevated temperature followed by reverse phase chromatography performed in the presence of a water miscible organic modifier and at an elevated temperature.

17 Claims, 2 Drawing Sheets
Specification includes a Sequence Listing.

```
                           SEQUENCE LISTING

<160> NUMBER OF SEQ ID NOS: 6

<210> SEQ ID NO 1
<211> LENGTH: 21
<212> TYPE: PRT
<213> ORGANISM: Homo Sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial
<220> FEATURE:
<223> OTHER INFORMATION: Insulin glargine A chain

<400> SEQUENCE: 3

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 4
<211> LENGTH: 32
<212> TYPE: PRT
<213> ORGANISM: artificial sequence
<220> FEATURE:
<223> OTHER INFORMATION: Insulin glargine B chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 5
<211> LENGTH: 30
<212> TYPE: PRT
<213> ORGANISM: artificial sequence
<220> FEATURE:
<223> OTHER INFORMATION: Insulin lispro B chain

<400> SEQUENCE: 5

Phe Val Asn Gln His Leu Cys Gly Ser His Leu Val Glu Ala Leu Tyr
```

```
                1               5                   10                  15
Leu Val Cys Gly Glu Arg Gly Phe Phe Tyr Thr Lys Pro Thr
                        20                  25                  30

<210> SEQ ID NO 6
<211> LENGTH: 30
<212> TYPE: PRT
<213> ORGANISM: artificial sequence
<220> FEATURE:
<223> OTHER INFORMATION: Insulin glulisine B chain

<400> SEQUENCE: 6

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
                        20                  25                  30
```

PURIFYING INSULIN USING CATION EXCHANGE AND REVERSE PHASE CHROMATOGRAPHY IN THE PRESENCE OF AN ORGANIC MODIFIER AND ELEVATED TEMPERATURE

CROSS REFERENCE TO RELATED APPLICATIONS

This application is a continuation of U.S. Ser. No. 15/124,080 filed Sep. 7, 2016,as a National Stage of International Application No. PCT/US2015/019864 filed on Mar. 11, 2015, which claims the benefit under 35 U.S.C. 119(e) of U.S. Provisional Application No. 61/953,001, filed Mar. 14, 2014, both of which are incorporated herein by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "23742-US-CNT-SE-QTXT-23AUG2019.txt", creation date of Aug. 23, 2019, and a size of 3 KB. This sequence listing submitted via EFS-Web is part of the specification and is herein incorporated by reference in its entirety.

BACKGROUND OF THE INVENTION

(1) Field of the Invention

The present invention relates to a process for purifying insulin and insulin analogs that comprises high-pressure liquid chromatography with an acidic cation exchange medium performed in the presence of a water miscible organic modifier and at an elevated temperature followed by reverse phase chromatography performed in the presence of a water miscible organic modifier and at an elevated temperature.

(2) Description of Related Art

Recombinant production of insulin and insulin analogs in genetically modified microbial or yeast host cells entails expression of the insulin or insulin analog in the host cell as a single-chain precursor insulin molecule comprising three polypeptide domains (A-chain, C-chain, B-chain), as in native pro-insulins, along with the addition of a fusion peptide at the N-terminus whose function is to protect the nascent protein from internal degradation/modification during synthesis in the bacterial host, improve protein expression in the host, and to add a trypsin cleavage site that will render the correct amino acid, phenylalanine, at position B1, post-digest In the microbial host *E. coli*, the single-chain precursor insulin molecule is sequestered in inclusion bodies consisting of mostly of incorrectly folded single-chain precursor molecules. To produce recombinant insulin, the inclusion bodies are extracted from the cell, washed, and the single-chain precursor molecule is solubilized, refolded, and then purified by at least one chromatographic step. The refolded, single-chain precursor molecule is then further processed into insulin by the concurrent removal of the C-chain and the N-terminal fusion peptide by enzymatic digestion. Insulin is comprised of an A-chain and B-chain linked together by three disulfide bridges. In subsequent purification steps, including ion-exchange chromatography and reverse phase HPLC, insulin is purified away from digestion byproducts to yield a highly purified product. The purified product may be formulated in a zinc and m-cresol (preservative) containing buffer to provide the insulin drug product.

Methods for isolating inclusion bodies, refolding and enzymatically digesting precursor insulin molecules to produce insulin have been disclosed U.S. Pat. Nos. 5,663,291; 5,986,048; 6,380,355, and 5,473,049. Ion-exchange chromatography methods for purifying insulin from digestion byproducts have been disclosed in U.S. Pat. No. 5,101,013, which discloses cation-exchange chromatography on strongly acidic ion exchangers under atmospheric or medium pressure and elution by means of aqueous alkanol with only a relatively small amount of alkanol to purify insulin; and, U.S. Pat. No. 5,977,297, which discloses high-pressure cation-exchange chromatography on pressure-stable acidic cation exchangers under a pressure of about 1.1 MPa (11 bar) to about 40 MPa (400 bar) to purify insulin. Further purification of insulin has been described in U.S. Pat. Nos. 6,710,167 and 5,621,073.

While there are methods available for purifying insulin, there remains a need for alternative methods for purifying insulin and insulin analogs thereof.

BRIEF SUMMARY OF THE INVENTION

In an effort to provide additional processes for obtaining properly folded insulin or insulin analog from enzymatic cleavage reactions in high yield and pharmaceutically acceptable purity, we have found that insulin and insulin analogs may be purified from impurities and other byproducts of the enzymatic digestion by chromatography of a mixture comprising the insulin or insulin analog on an acid-stable cation exchange chromatography in the presence of a water miscible organic modifier and at an elevated temperature followed by reverse phase high performance liquid chromatography in the presence of a water miscible organic modifier and at an elevated temperature. In particular embodiments of the process, both chromatography steps are performed at an acidic pH. The two-step chromatographic process yields a pharmaceutically pure composition of the insulin or insulin analog. The process has a combined yield of about 65% or greater and provides a composition of the isolated insulin or insulin analog having a purity of about 99% or greater.

Therefore, the present invention provides a process for isolating properly folded insulin or insulin analogs from an aqueous mixture comprising the insulin or insulin analog and related impurities, wherein the process comprises (a) performing an acid-stable cation exchange chromatography with the aqueous mixture in the presence of a first water miscible organic modifier and at an elevated temperature to yield a first insulin or insulin analog mixture; and (b) performing a reverse phase high performance liquid chromatography on the first insulin or insulin analog mixture in the presence of a second water miscible organic modifier and at an elevated temperature to provide a second mixture comprising the properly folded insulin or insulin analog.

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the second mixture is obtained from the reverse phase high performance liquid chromatography using a linear gradient comprising the second water miscible organic modifier increasing in concentration from about 13 to 15 percent by volume to about 25 to 27 percent by volume. In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.0\%/CV$).

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa. In particular aspects of the process, the acid-stable cation exchange chromatography has an outlet temperature greater than room temperature; greater than 30° C.; greater than 40° C.; or a temperature between 41° C. to 45° C.; or about 42° C.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length. In particular aspects of the process, the reverse phase high performance liquid chromatography has an outlet temperature greater than room temperature; greater than 30° C.; greater than 40° C.; or a temperature between 40° C. to 46° C.; or about 43° C.

The present invention further provides a process for purifying a properly folded insulin or insulin analog from a mixture comprising the insulin or insulin analog and related impurities, the process comprising: (a) applying the mixture to an acid-stable cation exchange chromatography matrix; (b) washing the matrix with a first wash solution comprising a concentration of mineral salt of about 10 to 25 mM and a first water miscible organic modifier and then washing the matrix with a second wash solution comprising a concentration of mineral salt greater than the concentration of mineral salt in the first wash solution and less than the concentration of mineral salt capable of eluting the insulin or insulin analog from the matrix and the first water miscible organic modifier; (c) eluting the insulin or insulin analog from the matrix with an eluting solution comprising the concentration of mineral salt capable of eluting the insulin or insulin analog from the matrix and the first water miscible organic modifier to provide a second mixture; and (d) applying the second mixture to a reverse phase high performance liquid chromatography matrix and eluting the insulin or insulin analog with a linear gradient of a second water miscible organic modifier of increasing concentration from about 13 to 15 percent by volume to about 25 to 27 percent by volume to provide a mixture of the properly folded insulin or insulin analog; wherein the acid-stable cation exchange chromatography is at an outlet temperature greater than room temperature; greater than 30° C.; greater than 40° C.; or a temperature between 41° C. to 45° C.; or about 42° C. and the reverse phase high performance liquid chromatography is performed at an outlet temperature greater than room temperature; greater than 30° C.; greater than 40° C.; or a temperature between 40° C. to 46° C.; or about 43° C.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.0\%/CV$).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step: (d) applying the second mixture to a reverse phase high performance liquid chromatography matrix; washing the matrix with a first solution comprising about 4 to 7 percent of a second water miscible organic modifier; washing the matrix with a linear gradient of the second water miscible organic modifier of increasing concentration from about 4 to 7 percent by volume to about 13 to 15 percent by volume; and eluting the insulin or insulin analog with a linear gradient of a second water miscible organic modifier of increasing concentration from about 13 to 15 percent by volume to about 25 to 27 percent by volume to provide a mixture of the properly folded insulin or insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume (Δ12%/CV to Δ22%/CV). In a further aspect of the process, the process is performed on a column and the linear gradient is performed at a rate of change of about 18 percent of water miscible organic modifier per column volume (Δ18%/CV). In a further aspect of the process, the process is performed on a column and the linear gradient is from 5 percent to 11 percent by volume of water miscible organic modifier or performed at a rate of change of about 12 percent of water miscible organic modifier per column volume (Δ12%/CV).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl.

In a further aspect of the process, the mixture that is loaded onto the cation exchange chromatography matrix comprises from about 3.0 to about 26.0 g of protein per liter in a solution comprising a water miscible organic modifier. In a further aspect, the mixture comprises from 10 to about 50 percent by volume of a water miscible organic modifier. In a further aspect, the loading step is performed using an aqueous mixture which comprises from about 25 to about 35 percent or 30 percent by volume of a water miscible organic modifier. In particular aspects, the water miscible organic modifier is hexylene glycol.

In a further aspect of the process, the elution of the insulin or insulin analog is isocratic.

The present invention further provides a process for purifying a properly folded insulin or insulin analog from a mixture comprising the insulin or insulin analog and related impurities, the process comprising:
(a) a cation exchange chromatography step performed in a column under a column differential pressure of less than 1.1 MPa, or less than 1.0 MPa, or less than 0.5 MPa, or about 0.276 MPa and at an outlet temperature greater than room temperature; greater than 30° C.;

greater than 40° C.; or a temperature between 41° C. to 45° C.; or about 42° C., the steps comprising
  (i) applying the mixture to a cation exchange chromatography matrix in the column;
  (ii) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the insulin or insulin analog from the column and the first water miscible organic modifier;
  (iii) eluting the insulin analog from the matrix with an eluting solution comprising the concentration of mineral salt capable of eluting the insulin or insulin analog from the column and the first water miscible organic modifier to provide a second mixture; and
(b) a reverse phase high performance liquid chromatography being performed at an outlet temperature greater than room temperature; greater than 30° C.; greater than 40° C.; or a temperature between 40° C. to 46° C.; or about 43° C., the steps comprising
  (i) applying the second mixture to a reverse phase high performance liquid chromatography matrix and
  (ii) eluting the insulin or insulin analog with a linear gradient of a second water miscible organic modifier of increasing concentration from about 13 to 15 percent by volume to about 25 to 27 percent by volume to provide a mixture of the properly folded insulin or insulin analog.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta1.7\%/CV$ to $\Delta2.3\%/CV$). In a further aspect of the process, the process is performed on a column and the linear gradient is performed at a rate of change of about 2.0 percent of water miscible organic modifier per column volume ($\Delta2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta2.0\%/CV$).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (b) a reverse phase high performance liquid chromatography being performed at an outlet temperature greater than room temperature; greater than 30° C.; greater than 40° C.; or a temperature between 40° C. to 46° C.; or about 43° C., the steps comprising
  (i) applying the second mixture to a reverse phase high performance liquid chromatography matrix;
  (ii) washing the matrix with a first solution comprising about 4 to 7 percent of a second water miscible organic modifier;
  (iii) washing the matrix with a linear gradient of the second water miscible organic modifier of increasing concentration from about 4 to 7 percent by volume to about 13 to 15 percent by volume; and
  (iv) eluting the insulin or insulin analog with a linear gradient of a second water miscible organic modifier of increasing concentration from about 13 to 15 percent by volume to about 25 to 27 percent by volume to provide a mixture of the properly folded insulin or insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume ($\Delta12\%/CV$ to $\Delta22\%/CV$). In a further aspect of the process, the process is performed on a column and the linear gradient is performed at a rate of change of about 18 percent of water miscible organic modifier per column volume ($\Delta18\%/CV$). In a further aspect of the process, the process is performed on a column and the linear gradient is from 5 percent to 11 percent by volume of water miscible organic modifier or performed at a rate of change of about 12 percent of water miscible organic modifier per column volume ($\Delta12\%/CV$).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.6\%/CV$). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the insulin or insulin analog is eluted from the column with about 20 column volumes of the eluting solution.

In a further aspect of the process, the mixture that is loaded onto the cation exchange chromatography matrix comprises from about 3.0 to about 26.0 g of protein per liter in a solution comprising a water miscible organic modifier. In a further aspect, the mixture comprises from 10 to about 50 percent by volume of a water miscible organic modifier. In a further aspect, the loading step is performed using an aqueous mixture which comprises from about 25 to about 35 percent or 30 percent by volume of a water miscible organic modifier. In particular aspects, the water miscible organic modifier is hexylene glycol.

In a further aspect of the process, the elution of the insulin or insulin analog is isocratic.

In a further aspect of the process, the differential pressure is less than 1.1 MPa, less than 1.0 MPa, or less than 0.5 MPa, or about 0.276 MPa.

In further aspects of the process, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6 thus a pI shifted insulin analog has a pI greater than 5.6 or less than 5.4. In particular aspects the insulin analog has a pI from between 5.8 to 8.0. An acid-stable insulin analog such as insulin glargine has a pI of about 6.7 to 7.0. In a further aspect, the insulin analog is insulin glargine, insulin aspart, insulin glulisine, or insulin lispro. For chromatography of acid-stable insulins a weak cation material may be used and for chromatography for insulins with a pI similar to that of native insulin, a strong cation exchange material may be used.

In general, for insulin analogs with a pI greater than the pI of native insulin, the cation exchanger is a weak cation exchange and for insulin analogs with a pI similar to that of native insulin, the cation exchanger is a strong cation exchanger.

Definitions

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "insulin analog" as used herein includes any heterodimer analog that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; and/or deleting any or all of positions B1-4 and B26-30. Insulin analogs include molecules having one to 10 amino acids at the N or C terminus of the A-chain peptide and/or B-chain peptide. Insulin analogs further include molecules amidated at the C-terminus of the A-chain peptide and/or B-chain peptide. Examples of insulin analogs include but are not limited to the insulin analogs disclosed in published international application WO20100080606, WO2009/099763, and WO2010080609, the disclosures of which are incorporated herein by reference. Insulin glargine (Gly(A21), Arg(B31), Arg(B32)-human insulin: A-chain peptide SEQ ID NO:3; B-chain peptide SEQ ID NO:4), insulin lispro (Lys(B28), Pro(B29)-human insulin: A-chain peptide SEQ ID NO:1; B-chain peptide SEQ ID NO:5, insulin glusiline (Lys(B3), Glu(B29)-human insulin: A-chain peptide SEQ ID NO:1; B-chain peptide SEQ ID NO:6), and insulin detemir (Lys-myristic acid(B29)-human insulin: A-chain peptide SEQ ID NO:1; B-chain peptide SEQ ID NO:2 with B-29 acylated with myristic acid) are examples of commercially available insulin analogs.

The term "insulin analogs" further includes heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analog is a partial agonist that has from 2× to 100× less activity at the insulin receptor as does native insulin. In other aspects, the insulin analog has enhanced activity at the insulin receptor.

The term "properly folded" refers to insulin or insulin analogs in which the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "pharmaceutically pure" refers to an insulin or insulin analog that is greater than 99 percent pure with respect to contaminating macromolecules, particularly other proteins and nucleic acids, and free of infectious and pyrogenic agents.

DETAILED DESCRIPTION OF THE INVENTION

Figure 1:
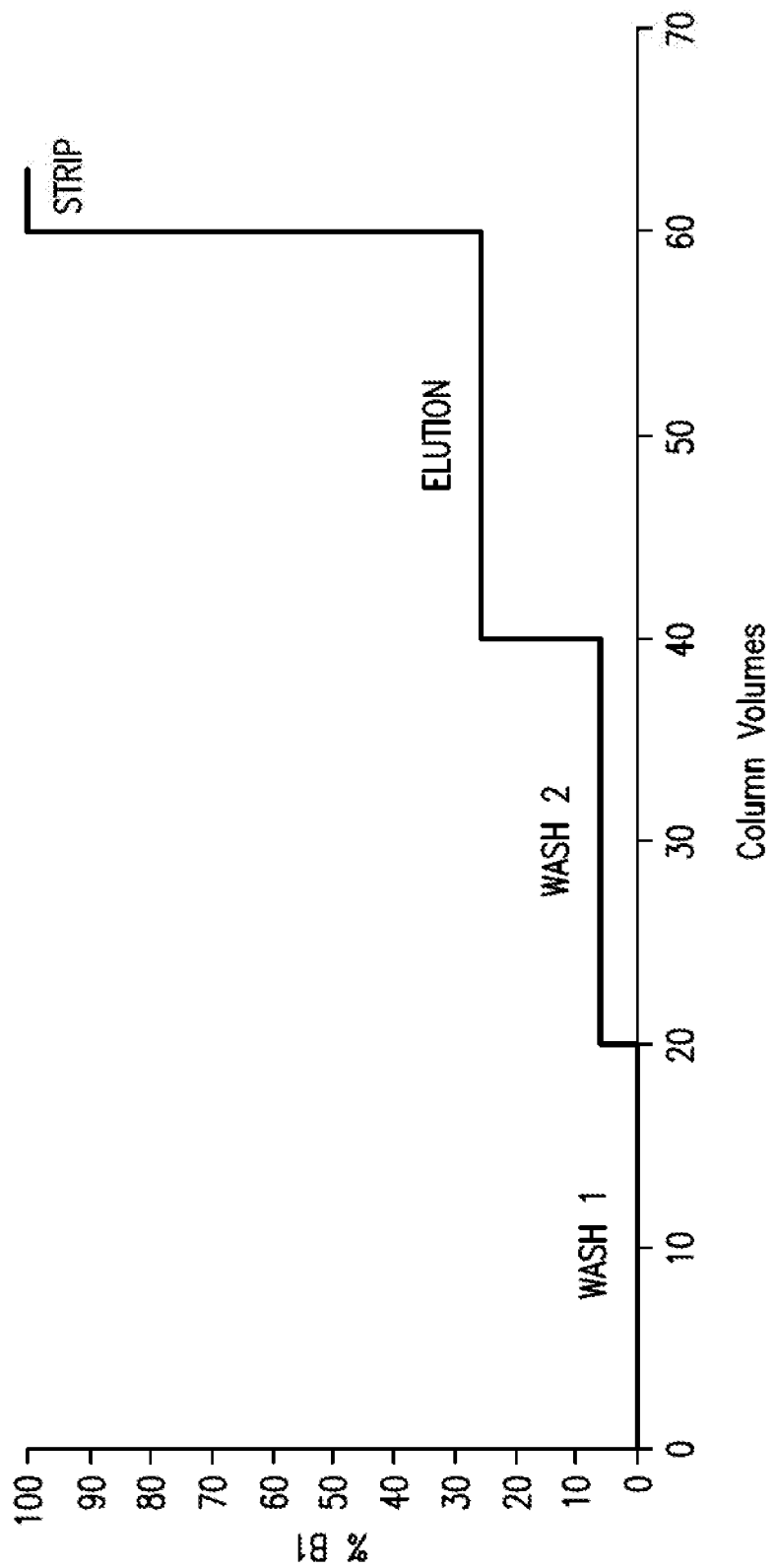
FIG. 1 shows a CEX chromatography gradient profile. Following loading of the insulin sample from an enzymatic digest in buffer A1, the column is washed with A1 buffer (Wash 1) for 20 column volumes. Next, the column is washed with Wash 2 containing an A1/B1 mixture (about 6.5% B1) for 20 column volumes as shown. The insulin sample is eluted with an A1/B1 mixture (about 26% B1) for twenty column volumes as shown. The column is stripped using B1 buffer.

Precursor insulin or insulin analog molecules produced in prokaryote host cells such as *E. coli* or lower eukaryote host cells such as *Saccharomyces cerevisiae* or *Pichia pastoris* are enzymatically cleaved in vitro to remove the connecting peptide joining the B-chain peptide to the A-chain peptide to produce insulin or an insulin analog. The enzymatic cleavage of precursor insulin or insulin analog molecules is using achieved by digestion with trypsin, carboxypeptidase, lysC, or combinations thereof. However, the enzymatic digests introduce impurities such as miscleaved protein, the three amino acid B-chain truncate (des-Thr), deamidoinsulin, arginine- and diarginine-insulin and insulin ethyl ester. In addition, precursor insulin or insulin analog molecules produced in prokaryote host cells are not properly folded, therefore, the precursor molecules are subjected to a refold reaction prior to the enzymatic digest to refold the molecules into the proper tertiary conformation. However, a portion of the molecules from the refold reaction are misfolded and need to be removed. In addition, some molecules may include amino acid misincorporations and need to be removed as well.

To remove these impurities, the present invention provides a two-step chromatography process that is capable of providing pharmaceutically pure compositions of the insulin or insulin analog has been developed. In the first step, a mixture comprising the insulin or insulin analog molecules is subjected to acid-stable cation exchange chromatography in the presence of a water miscible organic modifier and at an elevated temperature. The insulin or insulin analog recovered from the first step is subjected to reverse phase high performance liquid chromatography in the presence of a water miscible organic modifier and at an elevated temperature. The two-step chromatographic process yields a pharmaceutically pure composition of the insulin or insulin analog. The process has a combined yield of about 65% or greater and provides a composition of the isolated insulin or insulin analog having a purity of about 99% or greater.

Cation Exchange Chromatography

The cation exchange chromatography process may be performed in a column chromatography format in which during the chromatography the column differential pressure is less than 1.1 MPa and the outlet temperature is at an outlet temperature greater than room temperature; greater than 30° C.; greater than 40° C.; or a temperature between 41° C. to 45° C.; or about 42° C. In particular aspects, the differential pressure is less than 1.0 MPa. In a particular aspect, the differential pressure may be about 1.1 MPa to about 40 MPa as disclosed in U.S. Pat. No. 5,977,297.

The acidic cation exchange material may be a temperature-stable acid cation exchange material, which in a further still aspect, may be a high-capacity hydrogel polymerized within the pores of a rigid ceramic bead and cross-linked to sulfo groups on the beads, for example, BioSepra CM Ceramic HyperD F ceramic beads comprising a highly substituted hydrogel comprising carboxymethyl functional groups therein (available from Pall Corporation, Port Washington, N.Y.) is a weak cation exchanger whereas BioSepra S Ceramic HyperD F ceramic beads comprising a highly substituted hydrogel comprising sulfonic acid functional groups therein (available from Pall Corporation, Port Washington, N.Y.) is a strong cation exchanger. In other aspects, the temperature-stable acidic cation exchange material may be a copolymer of polystyrene and divinylbenzene, which has been modified with sulfo groups. Thus, acidic cation exchange materials that may be used in the process include but are not limited to BioSepra CM Ceramic HyperD F ceramic beads comprising a highly substituted hydrogel therein, which are available from Pall Corporation, Port Washington, N.Y.; BioSepra CM Ceramic HyperD F ceramic beads comprising a highly substituted hydrogel therein, which are available from Pall Corporation, Port Washington, N.Y.; Source 30S or 15S polystyrene/divinyl benzene polymer resins, which are available from GE Healthcare Life Sciences, Pittsburgh, Pa.; POROS 50 μm resins, which are available from Life Technologies, Carlsbad, Calif.), and MACROPREP 50 μm methacrylate resins, which are available from by Biorad Corp. (Hercules, Calif.).

The acidic cation exchange material may be packed into a column for chromatography using known, conventional methods. In general, the acidic cation exchange material is equilibrated in a strip/storage buffer solution and then packed into a column. After the column is packed with the acidic cation exchange material, the column is briefly flushed with a cleaning solution comprising a base, for example NaOH, as a pre-use sanitization step and then promptly flushed with a pre-equilibration solution followed by the strip/storage solution. The acidic cation exchange material should be exposed to the cleaning solution and the pre-equilibration solution for as little time as possible to reduce downstream pressure issues from occurring during the purification of insulin or insulin analog.

In general, the eluents (strip/storage solution, pre-equilibration solution, and elution solution) comprise a buffer substance, water, and organic modifiers. Suitable buffer substances include phosphates, alkali metal or alkaline earth metal salts, such as potassium acetate, ammonium citrate, sodium citrate, acetate, sulfate or chloride.

The eluents further contain water-miscible organic modifiers such as alcohols, ketones, methyl acetate, dioxane, or acetonitrile. Alcohols such as hexylene glycol, n- or iso-propanol, methanol, ethanol, or butanol may be used as the water-miscible organic modifier. The concentration of the water-miscible organic modifier for the chromatography is from about 10 to about 50% by volume, from about 20 to about 40% by volume, or from about 25 to about 35% by volume. The concentration of the buffer substance is from about 1 mM to about 100 mM, about 10 to 50 mM, or about 50 mM, or about 20 mM. Further additives include a physiologically tolerated mineral salt such as NaCl and may include one or more organic acids such as formic acid, acetic acid, lactic acid or citric acid, a base, e.g., NaOH, and/or preservatives. The pH of the buffer solution comprising the buffer substance is from about 2.5 to about 5.5. In particular aspects, the pH is about 5.1.

In general, the pre-equilibration solution will comprise a buffer solution; the equilibration solution will comprise a buffer solution, a water-miscible organic modifier, and a mineral salt, for example NaCl; the strip/storage solution will comprise a buffer solution, a water-miscible organic modifier, and an amount of mineral salt; for example NaCl greater than the amount in the equilibration solution and of a concentration sufficient to remove any proteins or impurities bound to the acidic cation exchange material in the column, e.g., about 10 to 25 times, about 12.5 times the amount of mineral salt in the equilibration solution.

Loading the column, chromatography, and elution of the insulin or insulin analog is achieved using known, conventional technical methods. The loading of the column with a loading solution comprising the insulin or insulin analog to be purified may have a protein content of about 3.0 to 26.0 grams of insulin or insulin analog per liter of acidic cation exchange material. In general, the loading of the acidic cation exchange material may be achieved by dissolving the insulin or insulin analog mixture in a buffer solution similar to the equilibration buffer for the acidic cation exchange material as described herein to provide a sample solution. In particular aspects, the insulin or insulin analog is provided in a sample solution with a pH of about 3.5 to 5.1, or about 4.2, at a concentration of about 1 to 2 g/L, which may further include a water miscible organic modifier. In particular aspects, the sample solution comprises from 10 to about 50 percent by volume of a solution comprising a water miscible organic modifier. In a further aspect, the loading step is performed using an aqueous mixture which comprises from about 25 to about 35 percent by volume of a solution comprising a water miscible organic modifier. In particular aspects, the water miscible organic modifier is hexylene glycol.

Following the loading of the insulin or insulin analog onto the column, the column is washed in a step-wise fashion with a first wash solution comprising a concentration of mineral salt of about 10 to 20 mM for at least four or five column volumes up to about 20 column volumes. The first wash may be followed by an optional step of washing the column with a second wash solution comprising a mineral salt at a concentration that is greater than the mineral salt concentration in the first wash solution and less than a mineral salt concentration capable of eluting the insulin or insulin analog from the column prior to eluting the insulin or insulin analog for at least 15 to 20 column volumes. Elution of the insulin or insulin analog is achieved by applying to the column an elution solution comprising a concentration of mineral salt capable of eluting the insulin or insulin analog from the column for at least 10 column volumes or for a time until the amount of insulin or insulin analog detected by UV monitoring in a fraction collected during the elution is about 10% of the peak fraction of insulin or insulin analog during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analog onto the column, the column is washed in a step-wise fashion with a first wash solution comprising about 18 to 22 mM of a mineral salt for at least five to 10 column volumes, which may be followed by an optional second wash with a second wash solution comprising about 35 to 39 mM of a mineral salt for at least 10 column volumes. Elution of the insulin or insulin analog is achieved by applying to the column an elution solution comprising about 80 to 100 mM of a mineral salt for at least 10 column volumes or for a time until the amount of insulin or insulin analog detected by UV monitoring in a fraction during the elution is about 10% of the peak fraction of insulin or insulin analog during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analog onto the column, the column is washed in a step-wise fashion with a first wash solution comprising about 18 to 22 mM of a mineral salt for about 18 to 20 column volumes, which may followed by an optional second wash with a second wash solution comprising about 35 to 39 mM of a mineral salt for about 18 to 20 column volumes. Elution of the insulin or insulin analog is achieved by applying to the column an elution solution comprising about 80 to 100 mM of a mineral salt for 18 to 20 column volumes or for a time until the amount of insulin or insulin analog detected by UV monitoring in a fraction during the elution is about 10% of the peak fraction of insulin or insulin analog during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analog onto the column, the column is washed in a step-wise fashion with a first wash solution comprising about 18 to 22 mM of a mineral salt for at least five to 10 column volumes, which may be followed by an optional second wash with a second wash solution comprising about 35 to 39 mM of a mineral salt for at least 10 column volumes. Elution of the insulin or insulin analog is achieved by applying to the column an elution solution comprising about 93 to 97 mM of a mineral salt for at least 10 column volumes or for a time until the amount of insulin or insulin analog detected by UV monitoring in a fraction during the elution is about 10% of the peak fraction of insulin or insulin analog during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analog onto the column, the column is washed in a step-wise fashion with a first wash solution comprising about 18 to 22 mM of a mineral salt for about 18 to 20 column volumes, which may followed by an optional second wash with a second wash solution comprising about 35 to 39 mM of a mineral salt for about 18 to 20 column volumes. Elution of the insulin or insulin analog is achieved by applying to the column an elution solution comprising about 93 to 97 mM of a mineral salt for 18 to 20 column volumes or for a time until the amount of insulin or insulin analog detected by UV monitoring in a fraction during the elution is about 10% of the peak fraction of insulin or insulin analog during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analog onto the column, the column is washed in a step-wise fashion with a first wash solution comprising 20 mM±2.5 mM of a mineral salt for about 18 to 20 column volumes, which may optionally be followed by a second wash with a second wash solution comprising 37 mM±2.5 mM of a mineral salt for about 18 to 20 column volumes. Elution of the insulin or insulin analog is achieved by applying to the column an elution solution comprising 95 mM±2.5 mM of a mineral salt for 18 to 20 column volumes or for a time until the amount of insulin or insulin analog detected by UV monitoring in a fraction during the elution is about 10% of the peak fraction of insulin or insulin analog during the elution as determined by UV monitoring. Yield may be monitored by measuring UV absorbance of fractions collected during the elution and purity may be determined by HPLC. The mineral salt may be NaCl.

The temperature during the chromatography and elution is greater than 20° C. or 30° C. or greater than 40° C. In particular embodiments, the temperature during the chromatography and elution may be about 25° C. to about 50° C. or from about 37° C. to about 47° C. In particular embodiments, the temperature during the chromatography and elution is greater than greater than 40° C. In particular aspects, the temperature during the chromatography and elution is about 42° C. or more or about 42° C. to about 47° C. In particular aspects, the temperature during the chromatography and elution is about 42° C. or at least 42° C. Preferably, the temperature is kept constant or nearly constant over the course of the chromatography and elution. The operating pressure during the chromatography and elution is substantially constant. The chromatography and elution may be carried out using a column differential pressure that is less than 1.1 MPa, less than 1.0 MPa, less than 0.5 MPa, or about 0.276 MPa. The eluent flow rates may be from about 182 to about 201 cm/hour.

In another aspect, the elution may be performed with a mineral salt gradient over time, for example, by a low mineral salt concentration being present in the elution buffer at the start of the elution (which initially can be zero percent salt) and by increasing the mineral salt concentration during the elution process. In particular aspects, the mineral salt may be NaCl. The operating temperature and pressure during the chromatography is substantially constant. The chromatography may be carried out using a column differential pressure that is less than 1.1 MPa, less than 1.0 MPa, less than 0.5 MPa, or about 0.276 MPa and at a temperature of about 25° to about 50° C., or of about 38° to about 50° C., or of about or at least 42° C. or more, or of about 42° to about 47° C., or of about 42° C., or at least 42° C. Yield may be monitored by measuring UV absorbance and purity may be determined by HPLC. In particular aspects, the first wash solution, the optional second wash solution, and the elution solution, each comprises from 10 to about 50 percent by volume of a water miscible organic modifier. In a further aspect, the loading step is performed using an aqueous mixture which comprises from about 25 to about 35 percent by volume of a water miscible organic modifier. In particular aspects, the water miscible organic modifier is hexylene glycol.

In further aspects of the process disclosed herein, the first and second wash steps and the eluting steps are performed using a first, second, and eluting solution, each comprising an aqueous mixture having about 25 to about 35 percent by volume of a water miscible organic modifier, which in a further aspect, the first and second wash steps and the eluting step are performed using an aqueous mixture which comprises from about 30 percent by volume of a water miscible organic modifier. In a further aspect of the process, the water miscible organic modifier is hexylene glycol.

Reverse Phase High Performance Liquid Chromatography

The reverse phase high performance liquid chromatography process may be performed in a column chromatography format.

The reverse phase high performance liquid chromatography may be performed with a temperature stable and pressure stable organic modified chromatography material or matrix. The material may be a lipophilically modified silica gel to which a hydrophobic matrix has been applied. Examples of a hydrophobic matrix are alkanes with a chain length of from 3 to 20 carbon atoms, in particular 8 to 18 carbon atoms. Additionally, the particle size can vary within a wide range, for example from 5 to 300 μm or 5 to 60 μm, in particular from 10 to 50 μm. The pore width can also vary within a wide range; favorable pore widths are from 50 to 300 Å, in particular 100 to 200 Å. Examples of lipophilically modified silica gel materials are: NUCLEOSIL, Macherey & Nagel GmbH+Co.KG, Duren, Germany spherical and non-spherical materials of various particle size up to 45 μm, 100 Å pore width, C8- or C18-modified; LICHROPREP, E. Merck Co., Darmstadt, Germany non-spherical and spherical materials of various particle sizes up to μm, 60-250 Å pore width, C8- or C18-modified; LICHROSPHER SELECT B, E. Merck Co., Darmstadt, Germany spherical material up to 25 μm particle size, C8-modified; WATERS PREP, Millipore GmbH, Eschborn, Germany C18-modified, 50-105 μm non-spherical, 100 Å pore width; ZORBAX PRO10, DuPont de Nemours (Germany) GmbH, Bad Homburg, Germany C8-modified, 10 μm, spherical, 100 Å pore width; and KROMASIL, EKA Nobel Co., Nobel Industries, Sweden C4-, C8- and C18-modified, up to 20 μm, spherical, 100, 150 or 200 Å pore width. In particular aspects, the chromatography material is a silica-based reverse phase resin modified with hydrocarbon chains about 8 carbons in length. In a further aspect, the chromatography material is KROMASIL C8-modified.

The reverse phase material may be packed into a column for chromatography using known, conventional methods. In general, the reverse phase material is equilibrated in a strip/storage buffer solution and then packed into a column. After the column is packed with the reverse phase material, the column is briefly flushed with a cleaning solution comprising a base, for example NaOH, as a pre-use sanitization step and then promptly flushed with a pre-equilibration solution followed by the strip/storage solution.

In general, the eluents (strip/storage solution, pre-equilibration solution, and elution solution) comprise a buffer substance, water, and water miscible organic modifier. Suitable buffer substances include phosphates, alkali metal or alkaline earth metal salts, such as potassium acetate, ammonium acetate, sodium citrate, acetate, sulfate or chloride.

The eluents further contain a water-miscible organic modifier such as alcohol, ketone, methyl acetate, dioxane, or acetonitrile. Alcohols such as hexylene glycol, n- or iso-propanol, methanol, ethanol, or butanol may be used as the water miscible organic modifier. The concentration of the buffer substance is from about 90 mM to about 110 mM, or about 100 mM. The pH of the buffer solution comprising the buffer substance is from about 2.8 to about 3.2. In particular aspects, the pH is about 3.0.

In general, the pre-equilibration solution will comprise a buffer solution; the equilibration solution will comprise a buffer solution and a water-miscible organic modifier at a concentration of about 4 to 7 percent per volume.

Loading the column, chromatography, and elution of the insulin or insulin analog is achieved using known, conventional technical methods. The loading of the column with a loading solution comprising the insulin or insulin analog to be purified may have a protein content of about 3.0 to 48 grams of insulin or insulin analog per liter of reverse phase material. In general, the loading of the reverse phase material may be achieved by diluting the eluent from the cation exchange chromatography comprising the insulin or insulin analog mixture with about 2.8 to 5.2 volumes, or about 4 volumes of water to provide a sample solution.

Following the loading of the insulin or insulin analog onto the column, the column is washed in with a first wash solution comprising a buffer comprising about 4 to 7 percent per volume of a water miscible organic modifier for at least three column volumes. The column wash is followed with a second wash. The second wash is applied as a liner gradient from about 4 to 7 percent to 13 to 15 percent per volume of a water miscible organic modifier in a buffer. Elution of the insulin or insulin analog is achieved by applying to the column an elution solution comprising a liner gradient from about 13 to 15 percent to 25 to 27 percent per volume of a water miscible organic modifier in a buffer. Elution of the insulin or insulin analog is detected by UV monitoring. Yield may be monitored by measuring UV absorbance of fractions collected during the elution and purity may be determined by HPLC.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume ($\Delta 12\%/CV$ to $\Delta 22\%/CV$). In a further aspect of the process, the process is performed on a column and the linear gradient is performed at a rate of change of about 18 percent of water miscible organic modifier per column volume ($\Delta 18\%/CV$). In a further aspect of the process, the process is performed on a column and the linear gradient is from 5 percent to 11 percent by volume of water miscible organic modifier or performed at a rate of change of about 12 percent of water miscible organic modifier per column volume ($\Delta 12\%/CV$).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.6\%/CV$). The temperature during the chromatography and elution is greater than room temperature or 30° C. or greater than 40° C. In particular embodiments, the temperature during the chromatography and elution may be about 25° C. to about 50° C. or from about 37° C. to about 47° C. In particular embodiments, the temperature during the chromatography and elution is greater than greater than 40° C. In particular aspects, the temperature during the chromatography and elution is about 43° C. or more or about 43° C. to about 47° C. In particular aspects, the temperature during the chromatography and elution is about 43° C. or at least 43° C. Preferably, the temperature is kept constant or nearly constant over the course of the chromatography and elution. The operating pressure during the chromatography and elution is substantially constant. The chromatography and elution may be carried out using a column differential pressure that is 5.5 MPa or less.

Concentrating the insulin or insulin analog obtained from the reverse phase chromatography may be achieved by precipitation with zinc salt or by crystallization using methods known in the art. The resulting insulin precipitates may be isolated by decantation, centrifugation, or filtration, and then dried. The present invention is suitable not only for analytical chromatography but also for preparative chromatography, in particular when the process according to the invention is carried out with a preparative high-pressure liquid chromatography (HPLC) system. Thus, the present invention may be used in a process for preparing insulin or insulin analog for use in treating diabetes.

Insulin Analogs

The insulin analog may be an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6 thus a pI shifted insulin analog has a pI greater than 5.6 or less than 5.4. In particular aspects the insulin analog has a pI from between 5.8 to 8.0. An acid-stable insulin analog such as insulin glargine has a pI of about 6.7 to 7.0. In a further aspect, the insulin analog is insulin glargine, insulin aspart, insulin glulisine, or insulin lispro. For chromatography of acid-stable insulins a weak cation material may be used and for chromatography for insulins with a pI similar to that of native insulin, a strong cation exchange material may be used.

Thus, in particular embodiments the present invention provides a process for isolating properly folded acid-stable insulin analog from an aqueous mixture comprising the acid-stable insulin analog and related impurities, wherein the process comprises (a) performing an acid-stable cation exchange chromatography with the aqueous mixture in the presence of a first water miscible organic modifier and at an elevated temperature to yield a first acid-stable insulin analog mixture; and (b) performing a reverse phase high performance liquid chromatography on the first acid-stable insulin analog mixture in the presence of a second water miscible organic modifier and at an elevated temperature to provide a second mixture comprising the isolated properly folded acid-stable insulin analog.

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the second mixture is obtained from the reverse phase high performance liquid chromatography using a linear gradient comprising the second water miscible organic modifier increasing in concentration from about 13 to 15 percent by volume to about 25 to 27 percent by volume. In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.6\%/CV$).

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa. In particular aspects of the process, the acid-stable cation exchange chromatography has an outlet temperature greater than room temperature; greater than 30° C.; greater than 40° C.; or a temperature between 41° C. to 45° C.; or about 42° C.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length. In particular aspects of the process, the reverse phase high performance liquid chromatography has an outlet temperature greater than room temperature; greater than 30° C.; greater than 40° C.; or a temperature between 40° C. to 46° C.; or about 43° C.

The present invention further provides a process for purifying a properly folded acid-stable insulin analog from a mixture comprising the acid-stable insulin analog and related impurities, the process comprising: (a) applying the mixture to a cation exchange chromatography matrix; (b) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the acid-stable insulin analog from the column and the first water miscible organic modifier; (c) eluting the acid-stable insulin analog from the column with an eluting solution comprising the concentration of mineral salt capable of eluting the acid-stable insulin analog from the column and the first water miscible organic modifier to provide a second mixture; and (d) applying the second mixture to a reverse phase high performance liquid chromatography matrix and eluting the acid-stable insulin analog with a linear gradient of a second water miscible organic modifier of increasing concentration from about 13 to 15 percent by volume to about 25 to 27 percent by volume to provide a mixture of the properly folded acid-stable insulin analog; wherein the acid-stable cation exchange chromatography is performed at an outlet temperature greater than room temperature; greater than 30° C.; greater than 40° C.; or a temperature between 41° C. to 45° C.; or about 42° C. and the reverse phase high performance liquid chromatography is performed at an outlet temperature greater than room temperature; greater than 30° C.; greater than 40° C.; or a temperature between 40° C. to 46° C.; or about 43° C.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.0\%/CV$).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (d): applying the second mixture to a reverse phase high performance liquid chromatography matrix; washing the matrix with a first solution comprising about 4 to 7 percent of a second water miscible organic modifier; washing the matrix with a linear gradient of the second water miscible organic modifier of increasing concentration from about 4 to 7 percent by volume to about 13 to 15 percent by volume; and eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume ($\Delta 12\%/CV$ to $\Delta 22\%/CV$). In a further aspect of the process, the process is performed on a column and the linear gradient is performed at a rate of change of about 18 percent of water miscible organic modifier per column volume ($\Delta 18\%/CV$). In a further aspect of the process, the process is performed on a column and the linear gradient is from 5 percent to 11 percent by volume of water miscible organic modifier or performed at a rate of change of about 12 percent of water miscible organic modifier per column volume ($\Delta 12\%/CV$).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.6\%/CV$). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analog is eluted from the column with about 20 column volumes of the eluting solution.

The present invention further provides a process for purifying a properly folded acid-stable insulin analog from a mixture comprising the acid-stable insulin analog and related impurities, the process comprising:
  (a) a cation exchange chromatography step performed in a column under a column differential pressure of less than 1.1 MPa, or less than 1.0 MPa, or less than 0.5 MPa, or about 0.276 MPa and at an outlet temperature greater than room temperature; greater than 30° C.; greater than 40° C.; or a temperature between 41° C. to 45° C.; or about 42° C., the steps comprising
    (i) applying the mixture to a cation exchange chromatography matrix in the column;
    (ii) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the acid-stable insulin analog from the column and the first water miscible organic modifier;
    (iii) eluting the acid-stable insulin analog from the matrix with an eluting solution comprising the concentration of mineral salt capable of eluting the acid-stable insulin analog from the column and the first water miscible organic modifier to provide a second mixture; and
  (b) a reverse phase high performance liquid chromatography being performed at an outlet temperature greater than room temperature; greater than 30° C.; greater than 40° C.; or a temperature between 40° C. to 46° C.; or about 43° C., the steps comprising
    (i) applying the second mixture to a reverse phase high performance liquid chromatography matrix and
    (ii) eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.0%/CV).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (b) a reverse phase high performance liquid chromatography being performed at an outlet temperature greater than room temperature; greater than 30° C.; greater than 40° C.; or a temperature between 40° C. to 46° C.; or about 43° C., the steps comprising
  (i) applying the second mixture to a reverse phase high performance liquid chromatography matrix;
  (ii) washing the matrix with a first solution comprising about 4 to 7 percent of a second water miscible organic modifier;
  (iii) washing the matrix with a linear gradient of the second water miscible organic modifier of increasing concentration from about 4 to 7 percent by volume to about 13 to 15 percent by volume; and
  (iv) eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume (Δ12%/CV to Δ22%/CV). In a further aspect of the process, the process is performed on a column and the linear gradient is performed at a rate of change of about 18 percent of water miscible organic modifier per column volume (Δ18%/CV). In a further aspect of the process, the process is performed on a column and the linear gradient is from 5 percent to 11 percent by volume of water miscible organic modifier or performed at a rate of change of about 12 percent of water miscible organic modifier per column volume (Δ12%/CV).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analog is eluted from the column with about 20 column volumes of the eluting solution.

In a further aspect of the process, the mixture that is loaded onto the cation exchange chromatography matrix comprises from about 3.0 to about 26.0 g of protein per liter in a solution comprising a water miscible organic modifier. In a further aspect, the mixture comprises from 10 to about 50 percent by volume of a water miscible organic modifier. In a further aspect, the loading step is performed using an aqueous mixture which comprises from about 25 to about 35 percent or 30 percent by volume of a water miscible organic modifier. In particular aspects, the water miscible organic modifier is hexylene glycol.

In a further aspect of the process, the elution of the acid-stable insulin analog is isocratic.

The present invention further provides a process for isolating properly folded pI-shifted insulin analog from an aqueous mixture comprising the pI-shifted insulin analog and related impurities, wherein the process comprises (a) performing an acid-stable cation exchange chromatography with the aqueous mixture in the presence of a first water miscible organic modifier and at an elevated temperature to yield a first pI-shifted insulin analog mixture; and (b) performing a reverse phase high performance liquid chromatography on the first pI-shifted insulin analog mixture in the presence of a second water miscible organic modifier and at an elevated temperature to provide a second mixture comprising the isolated properly folded pI-shifted insulin analog.

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the second mixture is obtained from the reverse phase high performance liquid chromatography using a linear gradient comprising the second water miscible organic modifier increasing in concentration from about 13 to 15 percent by volume to about 25 to 27 percent by volume. In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV).

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa. In particular aspects of the process, the acid-stable cation exchange chromatography has an outlet temperature greater than room temperature; greater than 30° C.; greater than 40° C.; or a temperature between 41° C. to 45° C.; or about 42° C.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length. In particular aspects of the process, the reverse phase high performance liquid chromatography has an outlet temperature greater than room temperature; greater than 30° C.; greater than 40° C.; or a temperature between 40° C. to 46° C.; or about 43° C.

The present invention further provides a process for purifying a properly folded pI-shifted insulin analog from a mixture comprising the acid-stable insulin analog and related impurities, the process comprising: (a) applying the mixture to a cation exchange chromatography matrix; (b) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the acid-stable insulin analog from the column and the first water miscible organic modifier; (c) eluting the acid-stable insulin analog from the column with an eluting solution comprising the concentration of mineral salt capable of eluting the acid-stable insulin analog from the column and the first water miscible organic modifier to provide a second mixture; and (d) applying the second mixture to a reverse phase high performance liquid chromatography matrix and eluting the acid-stable insulin analog with a linear gradient of a second water miscible organic modifier of increasing concentration from about 13 to 15 percent by volume to about 25 to 27 percent by volume to provide a mixture of the properly folded acid-stable insulin analog; wherein the acid-stable cation exchange chromatography is performed at an outlet temperature greater than room temperature; greater than 30° C.; greater than 40° C.; or a temperature between 41° C. to 45° C.; or about 42° C. and the reverse phase high performance liquid chromatography is performed at an outlet temperature greater than room temperature; greater than 30° C.; greater than 40° C.; or a temperature between 40° C. to 46° C.; or about 43° C.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.0\%/CV$).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (d): applying the second mixture to a reverse phase high performance liquid chromatography matrix; washing the matrix with a first solution comprising about 4 to 7 percent of a second water miscible organic modifier; washing the matrix with a linear gradient of the second water miscible organic modifier of increasing concentration from about 4 to 7 percent by volume to about 13 to 15 percent by volume; and eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume (Δ12%/CV to Δ22%/CV). In a further aspect of the process, the process is performed on a column and the linear gradient is performed at a rate of change of about 18 percent of water miscible organic modifier per column volume (Δ18%/CV). In a further aspect of the process, the process is performed on a column and the linear gradient is from 5 percent to 11 percent by volume of water miscible organic modifier or performed at a rate of change of about 12 percent of water miscible organic modifier per column volume (Δ12%/CV).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analog is eluted from the column with about 20 column volumes of the eluting solution.

The present invention further provides a process for purifying a properly folded pI-shifted insulin analog from a mixture comprising the acid-stable insulin analog and related impurities, the process comprising:
(a) a cation exchange chromatography step performed in a column under a column differential pressure of less than 1.1 MPa, or less than 1.0 MPa, or less than 0.5 MPa, or about 0.276 MPa and at an outlet temperature greater than room temperature; greater than 30° C.; greater than 40° C.; or a temperature between 41° C. to 45° C.; or about 42° C., the steps comprising
  (i) applying the mixture to a cation exchange chromatography matrix in the column;
  (ii) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the acid-stable insulin analog from the column and the first water miscible organic modifier;
  (iii) eluting the acid-stable insulin analog from the matrix with an eluting solution comprising the concentration of mineral salt capable of eluting the acid-stable insulin analog from the column and the first water miscible organic modifier to provide a second mixture; and
(b) a reverse phase high performance liquid chromatography being performed at an outlet temperature greater than room temperature; greater than 30° C.; greater than 40° C.; or a temperature between 40° C. to 46° C.; or about 43° C., the steps comprising
  (i) applying the second mixture to a reverse phase high performance liquid chromatography matrix and
  (ii) eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta 2.0\%/CV$).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (b) a reverse phase high performance liquid chromatography being performed at an outlet temperature greater than room temperature; greater than 30° C.; greater than 40° C.; or a temperature between 40° C. to 46° C.; or about 43° C., the steps comprising (i) applying the second mixture to a reverse phase high performance liquid chromatography matrix;

(ii) washing the matrix with a first solution comprising about 4 to 7 percent of a second water miscible organic modifier;

(iii) washing the matrix with a linear gradient of the second water miscible organic modifier of increasing concentration from about 4 to 7 percent by volume to about 13 to 15 percent by volume; and (iv) eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume ($\Delta 12\%/CV$ to $\Delta 22\%/CV$). In a further aspect of the process, the process is performed on a column and the linear gradient is performed at a rate of change of about 18 percent of water miscible organic modifier per column volume ($\Delta 18\%/CV$). In a further aspect of the process, the process is performed on a column and the linear gradient is from 5 percent to 11 percent by volume of water miscible organic modifier or performed at a rate of change of about 12 percent of water miscible organic modifier per column volume ($\Delta 12\%/CV$).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta 1.7\%/CV$ to $\Delta 2.3\%/CV$). In a further aspect of the process, the process is performed on a column and the linear gradient is performed at a rate of change of about 2.0 percent of water miscible organic modifier per column volume ($\Delta 2.0\%/CV$). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analog is eluted from the column with about 20 column volumes of the eluting solution.

In a further aspect of the process, the mixture that is loaded onto the cation exchange chromatography matrix comprises from about 3.0 to about 26.0 g of protein per liter in a solution comprising a water miscible organic modifier. In a further aspect, the mixture comprises from 10 to about 50 percent by volume of a water miscible organic modifier. In a further aspect, the loading step is performed using an aqueous mixture which comprises from about 25 to about 35 percent or 30 percent by volume of a water miscible organic modifier. In particular aspects, the water miscible organic modifier is hexylene glycol.

In a further aspect of the process, the elution of the pI-shifted insulin analog is isocratic.

The present invention further provides a process for isolating properly folded insulin glargine from an aqueous mixture comprising the insulin glargine and related impurities, wherein the process comprises (a) performing an acid-stable cation exchange chromatography with the aqueous mixture in the presence of a first water miscible organic modifier and at an elevated temperature to yield a first insulin glargine mixture; and (b) performing a reverse phase high performance liquid chromatography on the first insulin glargine mixture in the presence of a second water miscible organic modifier and at an elevated temperature to provide a second mixture comprising the isolated properly folded insulin glargine.

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the second mixture is obtained from the reverse phase high performance liquid chromatography using a linear gradient comprising the second water miscible organic modifier increasing in concentration from about 13 to 15 percent by volume to about 25 to 27 percent by volume. In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV).

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa. In particular aspects of the process, the acid-stable cation exchange chromatography has an outlet temperature greater than room temperature; greater than 30° C.; greater than 40° C.; or a temperature between 41° C. to 45° C.; or about 42° C.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length. In particular aspects of the process, the reverse phase high performance liquid chromatography has an outlet temperature greater than room temperature; greater than 30° C.; greater than 40° C.; or a temperature between 40° C. to 46° C.; or about 43° C.

The present invention further provides a process for purifying a properly folded insulin glargine from a mixture comprising the acid-stable insulin analog and related impurities, the process comprising: (a) applying the mixture to a cation exchange chromatography matrix; (b) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the acid-stable insulin analog from the column and the first water miscible organic modifier; (c) eluting the acid-stable insulin analog from the column with an eluting solution comprising the concentration of mineral salt capable of eluting the acid-stable insulin analog from the column and the first water miscible organic modifier to provide a second mixture; and (d) applying the second mixture to a reverse phase high performance liquid chromatography matrix and eluting the acid-stable insulin analog with a linear gradient of a second water miscible organic modifier of increasing concentration from about 13 to 15 percent by volume to about 25 to 27 percent by volume to provide a mixture of the properly folded acid-stable insulin analog; wherein the acid-stable cation exchange chromatography is performed at an outlet temperature greater than room temperature; greater than 30° C.; greater than 40° C.; or a temperature between 41° C. to 45° C.; or about 42° C. and the reverse phase high performance liquid chromatography is performed at an outlet temperature greater than room temperature; greater than 30° C.; greater than 40° C.; or a temperature between 40° C. to 46° C.; or about 43° C.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.0%/CV).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the acidic cation exchange chromatography is performed with a differential pressure of less than 1.1 MPa, less than 1.0 MPa, or less than 0.5 MPa, or about 0.276 MPa.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (d): applying the second mixture to a reverse phase high performance liquid chromatography matrix; washing the matrix with a first solution comprising about 4 to 7 percent of a second water miscible organic modifier; washing the matrix with a linear gradient of the second water miscible organic modifier of increasing concentration from about 4 to 7 percent by volume to about 13 to 15 percent by volume; and eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume ($\Delta$12%/CV to $\Delta$22%/CV). In a further aspect of the process, the process is performed on a column and the linear gradient is performed at a rate of change of about 18 percent of water miscible organic modifier per column volume ($\Delta$18%/CV). In a further aspect of the process, the process is performed on a column and the linear gradient is from 5 percent to 11 percent by volume of water miscible organic modifier or performed at a rate of change of about 12 percent of water miscible organic modifier per column volume ($\Delta$12%/CV).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume ($\Delta$1.7%/CV to $\Delta$2.3%/CV). In a further aspect of the process, the process is performed on a column and the linear gradient is performed at a rate of change of about 2.0 percent of water miscible organic modifier per column volume ($\Delta$2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume ($\Delta$2.6%/CV). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analog is eluted from the column with about 20 column volumes of the eluting solution.

The present invention further provides a process for purifying a properly folded insulin glargine from a mixture comprising the acid-stable insulin analog and related impurities, the process comprising:
 (a) a cation exchange chromatography step performed in a column under a column differential pressure of less than 1.1 MPa, or less than 1.0 MPa, or less than 0.5 MPa, or about 0.276 MPa and at an outlet temperature greater than room temperature; greater than 30° C.; greater than 40° C.; or a temperature between 41° C. to 45° C.; or about 42° C., the steps comprising
  (i) applying the mixture to a cation exchange chromatography matrix in the column;
  (ii) washing the matrix with a first wash solution comprising a concentration of mineral salt of about 10 to 25 mM and a first water miscible organic modifier and then washing the column with a second wash solution comprising a concentration of mineral salt greater than the concentration of mineral salt in the first wash solution and less than the concentration of mineral salt capable of eluting the acid-stable insulin analog from the column and the first water miscible organic modifier;
  (iii) eluting the acid-stable insulin analog from the matrix with an eluting solution comprising the concentration of mineral salt capable of eluting the acid-stable insulin analog from the column and the first water miscible organic modifier to provide a second mixture; and
 (b) a reverse phase high performance liquid chromatography being performed at an outlet temperature greater than room temperature; greater than 30° C.; greater than 40° C.; or a temperature between 40° C. to 46° C.; or about 43° C., the steps comprising
  (i) applying the second mixture to a reverse phase high performance liquid chromatography matrix and
  (ii) eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In a further aspect of the process, the linear gradient is performed on a column over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.0%/CV).

In particular aspects of the process, the first water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the first water miscible organic modifier is hexylene glycol. The first water miscible organic modifier may be at a concentration between 1 to 50 percent by volume or 20 to 50 percent by volume. In a further aspect, the first water miscible organic modifier may be at a concentration between 25 to 40 percent by volume. In a further aspect, the first water miscible organic modifier may be at a concentration between 5 to 30 percent by volume. In particular aspects, the water miscible organic modifier is at a concentration of about 30 percent by volume.

In particular aspects of the process, the second water miscible organic modifier is selected from acetonitrile, ketones, ethyl acetate, alcohols having 1 to 4 carbon atoms, and polyols having 3 to 6 carbon atoms. In particular aspects, the alcohol is selected from 1 or 2-propanol (n or iso-propanol), methanol, ethanol, and hexylene glycol. In a further aspect, the second water miscible organic modifier is isopropanol.

In particular aspects of the process, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In particular aspects of the process, the reverse phase high performance liquid chromatography is performed with a temperature stable and pressure stable organic modified chromatography material. In particular aspects, the chromatography material is a silica-based reverse phase resin modified with hydrocarbon chains 4 to 18 carbons in length. In a further aspect, the hydrocarbon chains are about 8 carbons in length.

In a further aspect of the process, in step (b) a reverse phase high performance liquid chromatography being performed at an outlet temperature greater than room temperature; greater than 30° C.; greater than 40° C.; or a temperature between 40° C. to 46° C.; or about 43° C., the steps comprising (i) applying the second mixture to a reverse phase high performance liquid chromatography matrix;
(ii) washing the matrix with a first solution comprising about 4 to 7 percent of a second water miscible organic modifier;
(iii) washing the matrix with a linear gradient of the second water miscible organic modifier of increasing concentration from about 4 to 7 percent by volume to about 13 to 15 percent by volume; and
(iv) eluting the insulin or insulin analog with a linear gradient of a second water miscible organic modifier of increasing concentration from about 13 to 15 percent by volume to about 25 to 27 percent by volume to provide a mixture of the properly folded acid-stable insulin analog.

In particular aspects of the process, the second wash is achieved using a linear gradient from about 4 to 7 percent to 13 to 15 percent per volume of a water miscible organic modifier in a buffer over a course of about 0.5 column volumes and at about a 10 minute residence time. In a further aspect of the process, the process is performed on a column and the linear gradient is performed at a rate of change of about 12 percent to 22 percent of water miscible organic modifier per column volume (Δ12%/CV to Δ22%/CV). In a further aspect of the process, the process is performed on a column and the linear gradient is performed at a rate of change of about 18 percent of water miscible organic modifier per column volume (Δ18%/CV). In a further aspect of the process, the process is performed on a column and the linear gradient is from 5 percent to 11 percent by volume of water miscible organic modifier or performed at a rate of change of about 12 percent of water miscible organic modifier per column volume (Δ12%/CV).

In particular aspects of the process, the elution is achieved using a linear gradient from about 13 to 15 percent to 25 to 27 percent per volume of a water miscible organic modifier in a buffer over a course of about 6 column volumes and at about a 10 minute residence time. In a further aspect of the process, the process is performed on a column and the linear gradient is performed at a rate of change of about 1.7 percent to 2.3 percent of water miscible organic modifier per column volume (Δ1.7%/CV to Δ2.3%/CV). In a further aspect of the process, the process is performed on a column and the linear gradient is performed at a rate of change of about 2.0 percent of water miscible organic modifier per column volume (Δ2.0%/CV). In a further aspect of the process, the process is performed on a column and the linear gradient is from 11 percent to 27 percent by volume of water miscible organic modifier or performed at a rate of change of about 2.6 percent of water miscible organic modifier per column volume (Δ2.6%/CV). In a further aspect of the process, the cation exchange chromatography first wash solution comprises a concentration of mineral salt of about 10 mM to about 20 mM, which in particular aspects may be NaCl. In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In particular aspects, the column is washed with about 5 to 20 volumes of the wash solution.

In a further aspect, the cation exchange chromatography second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the cation exchange chromatography eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analog is eluted from the column with about 20 column volumes of the eluting solution.

In a further aspect of the process, the mixture that is loaded onto the cation exchange chromatography matrix comprises from about 3.0 to about 26.0 g of protein per liter in a solution comprising a water miscible organic modifier. In a further aspect, the mixture comprises from 10 to about 50 percent by volume of a water miscible organic modifier. In a further aspect, the loading step is performed using an aqueous mixture which comprises from about 25 to about 35 percent or 30 percent by volume of a water miscible organic modifier. In particular aspects, the water miscible organic modifier is hexylene glycol.

In a further aspect of the process, the elution of the insulin glargine is isocratic.

able from Pall Corporation, Port Washington, N.Y.; Cat. No. 20050. The defined volume of cation exchange material is first allowed to settle. The storage solution (20% ethanol) is decanted and replaced with an equal volume of CEX Strip/Storage Solution (Table 1) and the cation exchange material is resuspended in this solution. Settling, decanting, and resuspension with an equal volume of CEX Strip/Storage Solution are repeated two more times allowing for the sufficient equilibration of the cation exchange material with 30% hexylene glycol.

Next, the slurry is diluted to achieve a slurry percent of about 50% and held in the CEX Strip/Storage Solution for 24 hours. The cation exchange material slurry is transferred to the column and resuspended with a paddle. The upper head plate is inserted into the column and lowered to the solution interface. The column is flow-packed with CEX Strip/Storage Solution at a flow rate that produces a column differential pressure of about 40 psid (0.276 MPA) or more and at a temperature of about 20±2° C. Once a stable bed height is achieved, the flow rate is reduced and the upper head plate is lowered until about 2 to 3 mm above the cation exchange material interface. The head space is to prevent the cation exchange material from interfering with the sealing of the head plate. The column is returned to the packing pressure, and the bed is allowed to compress again. The procedure of slowing flow and lowering the head plate is repeated as necessary until the upper head plate is about 2 to 3 mm above the resin cation exchange material interface at the packing pressure.

Next, the column is connected to the chromatography skid and flushed with CEX Cleaning Solution (Table 1) as a pre-use sanitization, during which a final compression of the bed is observed. If necessary, the head plate should be lowered again to remain 2 to 3 mm above the cation exchange material interface.

Next, the column is promptly flushed with CEX Pre-Equilibration Solution (Table 1) and CEX Strip/Storage Solution.

TABLE 1

CEX Chromatography Buffers & Raw Materials

| Buffers/Raw Material | Description |
|---|---|
| CEX Chromatography cation exchange material | BioSepra CM Ceramic HyperD F |
| CEX Load Diluent | Hexylene Glycol |
| CEX Pre-Equilibration Solution | 1M sodium acetate, pH 5.1 |
| CEX Equilibration/Wash 1 Solution (A1) | 20 mM sodium acetate, 20 mM sodium chloride, 30% hexylene glycol (v/v), pH 5.1 (before hexylene glycol addition) |
| CEX Strip/Storage Solution (B1) | 20 mM sodium acetate, 250 mM sodium chloride, 30% hexylene glycol (v/v), pH 5.1 (before hexylene glycol addition) |
| CEX Cleaning Solution | 0.5N sodium hydroxide |
| CEX Load Filter | Sartopore 2 (0.45/0.2 μm) MaxiCap Size 1 (0.6 m$^2$) |

The following examples are intended to promote a further understanding of the present invention.

EXAMPLE 1

The acidic cation exchange (CEX) column is packed with BioSepra CM Ceramic HyperD F, a high-capacity hydrogel polymerized within the pores of a rigid ceramic bead avail- Next, the column is equilibrated with CEX Equilibration/Wash 1 Solution (Table 1) using a gradient initially to transition from the CEX Strip/Storage Solution to the CEX Equilibration/Wash 1 Solution at column differential pressure of about 40 psid (0.276 MPa) or less with an outlet temperature of about 40±2° C. Next, the column is flushed with the defined volume of CEX Strip/Storage Solution and the (low-to-high) transition is monitored via conductivity. Finally, the column may be stored until use.

Crude recombinant insulin or insulin analog heterodimer obtained from a trypsin digest in 50 mM acetic acid, pH 3.5 is diluted to about 0.3 to 0.4 g/L with hexylene glycol prior to loading on the column and the pH adjusted to about 4.2. The mass of hexylene glycol to crude recombinant insulin is about 0.395 kg hexylene glycol/kg crude recombinant insulin. To prepare for loading of the diluted crude recombinant insulin, the column is equilibrated with CEX Equilibration/Wash 1 Solution using a gradient initially to transition from the CEX Strip/Storage Solution to the CEX Equilibration/Wash 1 Solution to prevent extreme pH excursions across the cation exchange material in the column. The column is loaded with the diluted crude recombinant insulin or insulin analog at about 3-6 g insulin or insulin analog/L cation exchange material/cycle. All steps between and including column wash and column strip use CEX Equilibration/Wash 1 Solution (A1) and CEX Strip/Storage Solution (B1) (Table 1). Following loading, the column is washed with CEX Equilibration/Wash 1 Solution containing about 20 mM NaCl.

The column is operated a flow rate that produces a column differential pressure of about 40 psid (0.276 MPa) or less with an outlet temperature of about 42±2° C. In general, the flow rate is about 182 to 201 cm/hour or about 1 L/minute. The column is washed as shown in FIG. 1 with an A1/B1 mixture containing about 6.5±1.0% solution B1 in solution A1 to produce a solution comprising about 37 mM NaCl for about 18-20 column volumes. The column is then eluted as shown in FIG. 1 with an A1/B1 mixture containing about 26.1±1.0% B1 in A1 to produce a solution comprising about 95 mM NaCl with about 20 column volumes. During elution, fractions are collected during the elution process to allow analysis by UV absorption prior to pooling of those fractions that contain eluted insulin or insulin analog. In general, collection of fractions begins at the start of the elution step and ends when the UV peak is below 10% of the peak maximum value. The fractions may be analyzed by HPLC to determine purity. The fractions that correspond to the required purity are combined. In general, purity as measured by HPLC is greater than 90% with a yield of about 60-85% or more.

A reverse phase (RP) high performance liquid chromatography column is packed with KROMOSIL. RP Chromatography materials are shown in Table 2. The column is then equilibrated at 43° C. using 5% Buffer B (5% isopropanol and 95% Buffer A). The column outlet temperature is controlled by an inline heat exchanger and column jacket. The column is stored in a solution of 30% Buffer A and 70% Buffer B prepared inline using the Step Operation: For processing, the RP load is prepared by diluting (inline) the CEX product pool 4× with water. During the process, UV absorbance is monitored at 295 nm.

Figure 2:
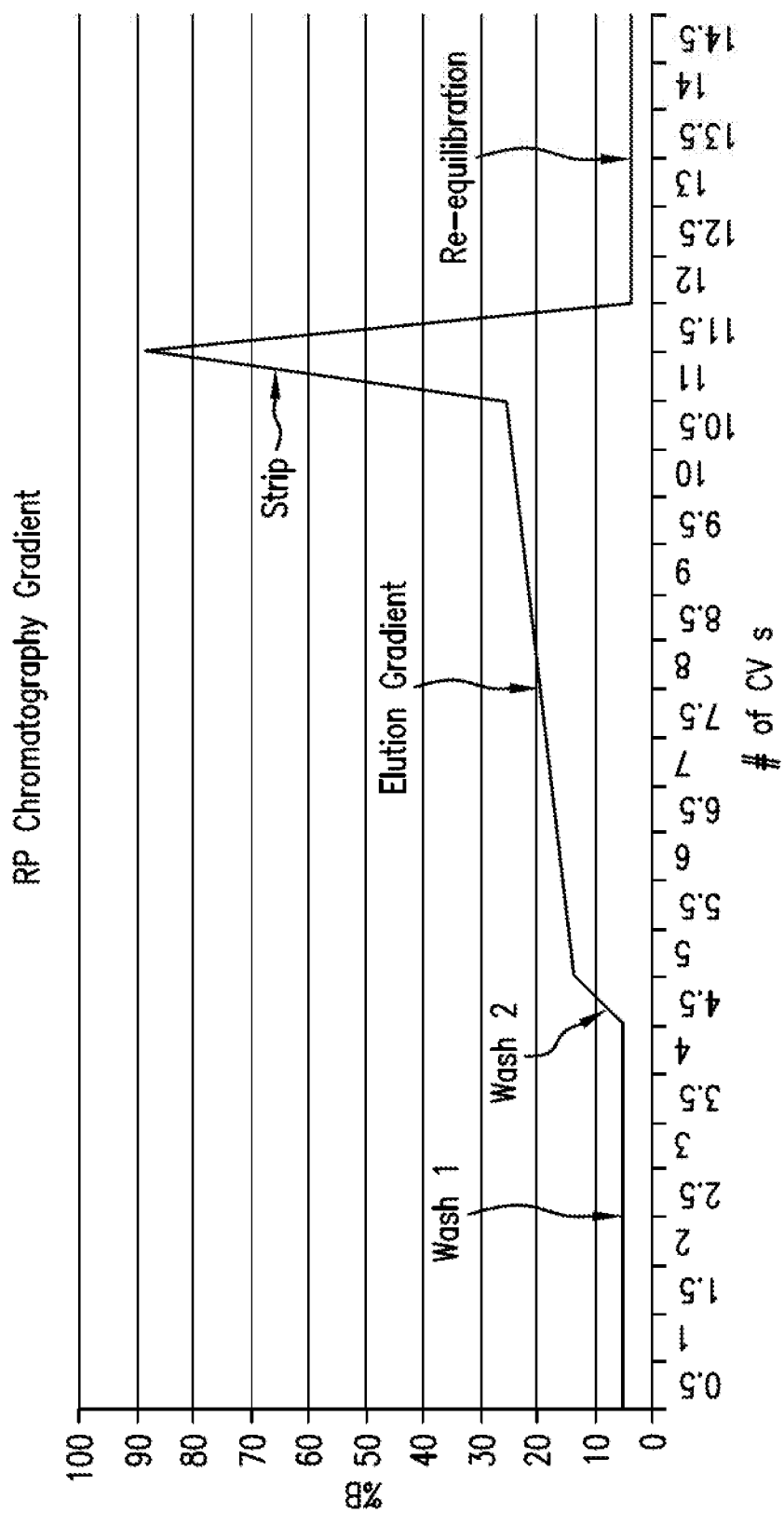
FIG. 2 shows a reverse phase high performance liquid chromatography profile. Following loading of the insulin sample from CEX chromatography, the column is washed with Wash 1 containing about 5% water miscible organic modifier. Next, the column is washed with Wash 2 containing a linear gradient of the water miscible organic modifier from 5% to 14%. The insulin sample is eluted with a linear gradient of the water miscible organic modifier from 14% to 26%.

The column is then loaded with diluted CEX pool to a defined load factor of about less than 24 g/L of protein. The column is then washed with Wash 1 followed by Wash 2. Wash 2 is a linear gradient of 5 to 14 percent isopropanol in Buffer A. The insulin or insulin analog product is then eluted with a linear gradient of 14 to 26% isopropanol in Buffer A. The product is collected based on A295 values into chilled water to reduce the isopropanol concentration in the product to less than 10%. Following elution, the column is stripped and re-equilibrated. The chromatography gradient used during the RP method from wash through re-equilibration is shown in FIG. 2.

TABLE 2

RP Chromatography Buffers & Raw Materials

| Buffers/Raw Material | Description |
| --- | --- |
| RP Chromatography material | Akzo Nobel KROMASIL 100-10-C8 resin (100 Å pore size, 10 µm particle size, C8 bonded phase) |
| Buffer A | 100 mM ammonium acetate, pH 3.0 |
| Buffer B | HPLC grade isopropanol (2-propanol, IPA) |
| Wash 1 | 95% Buffer A<br>5% Buffer B |
| Wash 2 | Start gradient: 95% Buffer A, 5% Buffer B<br>End gradient: 86% Buffer A, 14% Buffer B |
| Elution buffer | Start gradient: 86% Buffer A, 14% Buffer B<br>End gradient: 74% Buffer A, 26% Buffer B |

EXAMPLE 2

A crude mixture of the acid-stable insulin analog Gly(A21), Arg(B31), Arg(B32)-human insulin (insulin glargine) is purified as in Example 1. Because of non-specific enzymatic cleavages during the trypsin digest, very small amounts of product-related impurities, e.g. the three amino acid B-chain truncate (des-Thr) are produced. These product impurities, which are present in the crude mixture, are reduced using the method in Example 1. In general, the yield of the process has been about 65% with a purity of greater than 99.0% as determined by HPLC analysis.

Table of Sequences

| SEQ ID NO: | Description | Sequence |
| --- | --- | --- |
| 1 | Human insulin A chain | GIVEQCCTSICSLYQLENYCN |
| 2 | Human insulin B chain | FVNQHLCGSHLVEALYLVCGERGFFYTPKT |
| 3 | Insulin glargine A chain | GIVEQCCTSICSLYQLENYCG |
| 4 | Insulin glargine B chain | FVNQHLCGSHLVEALYLVCGERGFFYTPKTRR |
| 5 | Insulin lispro B chain | FVNQHLCGSHLVEALYLVCGERGFFYTKPT |
| 6 | Insulin glusiline B chain | FVKQHLCGSHLVEALYLVCGERGFFYTPET |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. A process for isolating properly folded insulin or insulin analog from an aqueous mixture comprising the insulin or insulin analog and related impurities, wherein the process comprises:
   (a) performing an acid-stable cation exchange chromatography with the aqueous mixture at a differential pressure of about 0.276 MPa in the presence of hexylene glycol at a concentration of about 30% by volume and at an outlet temperature between 41° C. to 45° C. under isocratic conditions to yield a first insulin or insulin analog mixture; and
   (b) performing a reverse phase high performance liquid chromatography with a silica-based reverse phase resin on the first insulin or insulin analog mixture in the presence of isopropanol and at an outlet temperature between 40° C. to 46° C. to provide a second mixture comprising the isolated properly folded insulin or insulin analog.

2. The process of claim 1, wherein the acid-stable cation exchange chromatography has an outlet temperature of about 42° C.

3. The process of claim 1, wherein the reverse phase high performance liquid chromatography has an outlet temperature of about 43° C.

4. The process of claim 1, wherein the insulin analog comprises an acid-stable insulin analog, which is stable and soluble in acidic or weakly acidic solutions and insoluble or partially insoluble at physiological pH.

5. The process of claim 4, wherein the acid-stable insulin analog comprises insulin glargine.

6. The process of claim 1, wherein the insulin analog comprises a pI-shifted insulin analog in which the pI of the insulin analog is less than or greater than the pI of native human insulin.

7. The process of claim 6, wherein the pI of the pI shifted insulin analog comprises a pI greater than 5.6 or less than 5.4.

8. The process of claim 6, wherein the pI-shifted insulin analog comprises a pI from between 5.8 to 8.0.

9. The process of claim 1, wherein the insulin analog comprises an insulin analog selected from the group consisting of insulin glargine, insulin aspart, insulin glulisine, and insulin lispro.

10. A process for purifying a properly folded insulin or insulin analog from a crude mixture comprising the insulin or insulin analog and related impurities, the process comprising:
   (a) providing a crude mixture of insulin or insulin analog in 50 mM acetic acid, pH 3.5 and diluting the crude mixture with hexylene glycol to about 0.3 to 0.4 g/L and then adjusting the pH to about 4.2 to produce a diluted crude mixture, wherein the mass of hexylene glycol to insulin or insulin analog in the diluted crude mixture is about 0.395 kg hexylene glycol/kg insulin or insulin analog;
   (b) applying the diluted crude mixture to a temperature-stable cation exchange chromatography matrix;
   (c) washing the matrix with a first wash solution comprising a concentration of mineral salt of about 10 to 25 mM and hexylene glycol at a concentration of about 30% by volume and then washing the matrix with a second wash solution comprising a concentration of mineral salt greater than the concentration of mineral salt in the first wash solution and less than the concentration of mineral salt capable of eluting the insulin or insulin analog from the matrix wherein the second wash solution comprises hexylene glycol at a concentration of about 30% by volume;
   (d) eluting the insulin or insulin analog from the matrix with an eluting solution comprising the concentration of mineral salt capable of eluting the insulin or insulin analog from the matrix and hexylene glycol at a concentration of about 30% by volume to provide a second mixture; the temperature-stable cation exchange chromatography being performed under a differential pressure of about 0.276 MPa and at an outlet temperature of about 42° C.; and
   (e) diluting the second mixture with water to provide a diluted second mixture comprising the insulin or insulin analog at a concentration of less than 24 g/L and applying the diluted second mixture to a reverse phase high performance liquid chromatography matrix comprising an acetate buffer at a pH of about 3.0 and isopropanol at a concentration of about 5% by volume; and
   eluting the insulin or insulin analog with a linear gradient of isopropanol in an acetate buffer at a pH of about 3.0 increasing concentration from about 13 to 15 percent by volume to about 25 to 27 percent by volume to provide a mixture of the properly folded insulin or insulin analog; the reverse phase high performance liquid chromatography being performed at an outlet temperature of about 43° C.

11. The process of claim 10, wherein step (e) further comprises washing the matrix with a first solution comprising about 4 to 7 percent by volume of isopropanol in an acetate buffer at a pH of about 3.0; and then washing the matrix with a linear gradient of the isopropanol in an acetate buffer at a pH of about 3.0 of increasing concentration from about 4 to 7 percent by volume to about 13 to 15 percent by volume.

12. The process of claim 10, wherein the insulin analog comprises an acid-stable insulin analog, which is stable and soluble in acidic or weakly acidic solutions and insoluble or partially insoluble at physiological pH.

13. The process of claim 12, wherein the acid-stable insulin analog comprises insulin glargine.

14. The process of claim 10, wherein the insulin analog comprises a pI-shifted insulin analog in which the pI of the insulin analog is less than or greater than the pI of native human insulin.

15. The process of claim 14, wherein the pI of the pI shifted insulin analog comprises a pI greater than 5.6 or less than 5.4.

16. The process of claim 14, wherein the pI-shifted insulin analog comprises a pI from between 5.8 to 8.0.

17. The process of claim 10, wherein the insulin analog comprises an insulin analog selected from the group consisting of insulin glargine, insulin aspart, insulin glulisine, and insulin lispro.

* * * * *